US005670659A

United States Patent [19]

Alas et al.

[11] Patent Number: 5,670,659
[45] Date of Patent: Sep. 23, 1997

[54] PREPARATION OF CITRACONIC ANHYDRIDE

[75] Inventors: Michel Alas, Melle; Alain Sigismondi, Lyons; Philippe-Jean Tirel, Communay, all of France

[73] Assignee: Rhone-Poulenc Chimie, Courbevoie Cedex, France

[21] Appl. No.: 380,722

[22] Filed: Jan. 30, 1995

[30] Foreign Application Priority Data

Jan. 28, 1994 [FR] France .................................. 94 00938

[51] Int. Cl.$^6$ ............................................. C07D 307/60
[52] U.S. Cl. ............................................. 549/261; 549/262
[58] Field of Search ................................. 549/261, 262

[56] References Cited

U.S. PATENT DOCUMENTS 3,833,619  9/1974  Baumann et al. ................... 260/346.8
4,639,531  1/1987  Baumann et al. ........................ 549/261

FOREIGN PATENT DOCUMENTS 0495544  7/1992  European Pat. Off. .

OTHER PUBLICATIONS

El–Anani, A. et al. *J. Chem. Soc., Perkins Trans. II*, pp. 1072–1077 (1973).

Katritzky, A.R. et al. *Comprehensive Heterocyclic Chemistry* vol. 2. (Pergamon Press, Oxford) p. 197 (1984).

Galanti, A.V. et al. *J. Polymer Sci., Polymer Chem. Ed.*, vol. 19, pp. 2243–2253 (1981).

Journal of Polymer Science, Polymer Chemistry Edition, vol. 19, 1981, New York, pp. 2243–2253 – A.V. Galanti et al, "Mechanism of Amine . . . ", p. 2243, p. 2249, table 1.

*Primary Examiner*—Mukund J. Shah
*Assistant Examiner*—King Lit Wong
*Attorney, Agent, or Firm*—Burns, Doane, Swecker & Mathis, L.L.P.

[57] ABSTRACT

Citraconic anhydride is prepared in a single step by heating itaconic acid, optionally in an inert organic solvent medium, in the presence of a catalytically effective amount of an at least partially organic acid/base catalyst compound having a pKa ranging from 4 to 10, in particular a salt catalyst such as pyridinium tosylate, itaconate or hydrochloride, ammonium itaconate, or phosphinium hydrobromide.

19 Claims, No Drawings

PREPARATION OF CITRACONIC ANHYDRIDE

BACKGROUND OF THE INVENTION

1. Field of the Invention

The present invention relates to a novel process for the preparation of citraconic anhydride and, more especially, to an improved single-step process for the preparation of citraconic anhydride from itaconic acid.

2. Description of the Prior Art

U.S. Pat. No. 2,966,498 describes the preparation of citraconic anhydride by heating itaconic acid at a temperature of from 165° C. to 190° C., in the presence of a catalyst comprising the dihydrogenophosphate of an alkali metal and an alkali metal sulfate. This technique is valuable because of the fact that citraconic anhydride is obtained in a single step, but it presents several disadvantages. Thus, the regulation of the temperature is difficult to ensure. The removal of the water formed in a minor amount during the reaction is difficult to carry out, and the distillation thereof also includes a fraction of the citraconic anhydride, which leads to a loss of product. Moreover, this type of process favors the polymerization of the citraconic anhydride. Lastly, the presence of a catalyst such as indicated above effects shielding in the reactor as soon as a large amount of catalyst is present.

Other processes for preparing citraconic anhydride are also known to this art. Thus, citraconic anhydride can be prepared by isomerization of itaconic anhydride. A. Galanti et al, *Journal of Polymer Science*, Polymer Chemistry Edition 19, 2243–2253 (1981) describe the isomerization of itaconic anhydride in the presence of an amine. Carrying out this reaction requires a first starting material, which is itaconic anhydride and which itself must be prepared from itaconic acid. Thus, two steps are unavoidably required.

SUMMARY OF THE INVENTION

Accordingly, a major object of the present invention is the provision of an improved single-step process for the preparation of citraconic anhydride that avoids or conspicuously ameliorates the above disadvantages and drawbacks to date characterizing the state of this art.

Briefly, the present invention features the preparation of citriconic anhydride by heating itaconic acid in the presence of an at least partially organic catalyst, of the acid-basic type, having a pKa ranging from 4 to 10.

DETAILED DESCRIPTION OF BEST MODE PREFERRED EMBODIMENTS OF THE INVENTION

More particularly according to the present invention, the characterizing feature thereof is the catalyst which permits citraconic anhydride to be obtained directly from itaconic acid.

Thus, it is essential that the catalyst be a salt having a pKa ranging from 4 to 10, preferably from 5 to 9; the pKa is defined as the co-logarithm of the dissociation constant of the acid measured in an aqueous medium, at 25° C.

The catalyst employed in the process according to the invention is meltable or melted in the reaction mass (or medium), and it is important that its melting point be preferably less than 200° C., and more preferably less than or equal to 180° C.

As indicated above, the catalyst is the reaction product of an acid with a base, with at least one of the two being an organic compound.

The catalyst can be a salt produced via the reaction of an acid with a base, which can be prepared at an earlier point in time.

The stoichiometric amounts of acid and base are typically used to form the salt.

The catalyst can also be a salt prepared in situ by the addition of acid and base to the reaction medium, or otherwise by the addition only of a base, the salt obtained resulting from the in situ reaction of the itaconic acid reactant and the base.

The catalyst can thus be prepared via the reaction of a mineral or organic acid with a base.

Exemplary such acids include halogenated acids such as hydrochloric acid, hydrobromic acid, hydrofluoric acid; halogenated or nonhalogenated oxyacids such as sulfuric acid, pyrosulfuric acid, perchloric acid, phosphoric acid; halogenated or nonhalogenated sulfonic acids such as fluorosulfonic acid, chlorosulfonic acid or trifluoromethanesulfonic acid, methanesulfonic acid, ethanesulfonic acid, ethanedisulfonic acid, benzenesulfonic acid, benzenedisulfonic acids, toluenesulfonic acids, naphthalenesulfonic acids and naphthalenedisulfonic acids.

Among the aforesaid acids, hydrochloric acid, hydrobromic acid, trifluoromethanesulfonic acid, paratoluenesulfonic acid and methanesulfonic acid are the preferred.

The itaconic acid can also be used for the preparation of the catalyst, as can other carboxylic acids that are nonvolatile under the conditions of the reaction.

The base is a duplet donor compound.

Primary, secondary or tertiary nitrogenous bases can thus be used, particularly:

(1) ammonia;

(2) primary amines such as n-propylamine, isopropylamine, isobutylamine, n-butylamine, tertiobutylamine, n-pentylamine, 2-methylbutylamine, 3-methylbutylamine, n-hexylamine, 2-ethylhexylamine, aniline, laurylamine, cyclohexylamine, cyclopentylamine, benzylamine, guanidine, acetamidine, ethanolamine, ethylenediamine, hexamethylenediamine, N-aminoethylpyrrolidine, pyrazoline, N-aminomorpholine, N-aminopiperidine, tetraethylenepentamine;

(3) secondary amines such as dibutylamine, dipropylamine, methylpropylamine, methylbutylamine, methylisobutylamine, methyltertiobutylamine, methylbenzylamine, ditertiobutylamine, diethanolamine, 1-methylcyclopentylamine, 1-methylcyclohexylamine, dicyclohexylamine, morpholine, imidazole, pyrrolidine, imidazolidine, piperazine, indole;

(4) tertiary amines such as triethyleneamine, tributylamine, dimethylaniline, pyridine, pyrazine, triethanolamine, tri(3,6-dioxaheptyl)amine, 1,8-diaza (5,4,0)bicyclo-7-undecene.

Among the compounds indicated above, the saturated or unsaturated tertiary nitrogenous heterocyclic bases, and preferably pyridine or pyrazine, are the preferred. The substituted derivatives thereof (α-picoline, β-picoline) can also be used.

Another category of bases suitable for use in the process according to the invention comprises the phosphines.

Trialkyl and triaryl phosphines are the preferred, particularly trimethylphosphine, triethylphosphine, tri-n-propylphosphine, tri-n-butylphosphine, tricyclohexylphosphine, triphenylphosphine, tritolylphosphine.

Specific examples of catalysts suitable for carrying out the process of the invention include:

Pyridinium tosylate,
Ammonium itaconate,
Pyridinium itaconate,
Pyridinium hydrochloride,
Phosphinium hydrobromide.

The amount of catalyst used in the process of the invention is such that it constitutes 0.1% to 30%, preferably 1% to 4%, of the weight of the itaconic acid.

The subject reaction can be carried out in the absence of any solvent, or in the presence of an organic solvent.

The selection of the solvent is determined according to its ability for solubilizing the initial itaconic acid.

Moreover, it must be inert under the conditions of the reaction.

It is preferable to use a liquid organic solvent that forms a binary azeotrope with water, the boiling point of which is generally at least 130° C. Said organic solvent is selected such that the binary azeotrope which it forms with water has a boiling point lower than:

(i) the boiling point of itaconic acid,
(ii) the boiling point of the binary azeotrope which the itaconic acid forms either with water or with the organic solvent itself.

Lastly, the organic solvent is preferably selected such that it does not form a ternary azeotrope with the itaconic acid and the water, in order to limit loss of such acid.

The organic solvents which are used in the process of the invention preferably have a boiling point ranging from 110° C. to 200° C., preferably from 130° C to 170° C.

Exemplary of such organic solvents are:

(1) aliphatic hydrocarbons, and more particularly paraffins such as, in particular, octane, isooctane, nonane, decane, undecane, tetradecane; aromatic hydrocarbons such as, particularly, toluene, xylenes, ethylbenzene, diethylbenzenes, trimethylbenzenes, cumene, pseudocumene, petroleum fractions constituted by an alkylbenzene mixture, particularly the Solvesso® type fractions;

(2) chlorinated aliphatic hydrocarbons such as, for example, 1,1,2-trichloroethane, pentachloroethane, 1-iodo-2-methylpropane, 1-chlorohexane, 1-chloro-2-ethylhexane, chlorinated aromatic hydrocarbons and more particularly chlorobenzene, chlorotoluenes;

(3) ethers, and more particularly aliphatic ethers such as, for example, butylether, isobutylether, ethylhexylether, 1-butoxy-2-methoxyethane, 1,1-diethoxybutane, amylether, isoamylether dipropoxymethane; aromatic ethers such as phenylpropylether, mesityl oxide;

(4) nitro compounds such as nitropropane, nitrobenzene.

The aromatic hydrocarbons, and more especially cumene and pseudocumene, are the preferred.

In the event that the organic solvent has too low a boiling temperature, it is possible to conduct the process according to the invention under pressure.

The temperature at which the reaction is carried out is generally the reflux temperature of the reaction mixture.

The temperature at which the reaction is carried out advantageously ranges from 130° C. to 180° C., and preferably from 150° C to 170° C.

When the water formed during the reaction is removed by azeotropic distillation, this distillation can be carried out continuously or discontinuously.

The water of the binary water/organic solvent azeotrope can be removed either by passing said azeotrope over a solid which absorbs water such as, for example, molecular sieves, before recycling, or by decanting.

After decanting the layer of heterogeneous azeotrope containing the major fraction of the water, the other layer can be recycled to the reaction mixture.

The concentration of itazonic acid in the reaction mixture (itaconic acid+organic solvent) is not critical. Normally, the acid constitutes 10% to 100%, preferably 10% to 50% of the weight of the reaction solvent.

In a preferred embodiment of the invention, the reaction is carried out in a controlled atmosphere of inert gases. An atmosphere of rare gases, preferably of argon, can be established, but it is more economical to use nitrogen.

From a practical standpoint, the reaction is indeed quite simple. The order of introduction of the reactants is not critical. Generally, the reaction solvent, the itaconic acid and the catalyst are charged. Heating is carried out to the desired temperature and the water formed is removed by azeotropic distillation throughout the reaction period.

The use of the catalyst according to the invention is particularly advantageous. In a preferred variation, during cooling the catalyst forms a bi-phasic system which permits it to be separated very easily, particularly by decanting.

After separation of the catalyst, the organic solvent is removed, preferably by distillation and the citraconic anhydride is recovered by conventional techniques, also preferably by distillation.

In order to further illustrate the present invention and the advantages thereof, the following specific examples are given, it being understood that same are intended only as illustrative and in nowise limitative.

In said examples to follow, the abbreviations TT and RR have the following definitions:

$$TT = \frac{\text{number of moles of itaconic acid converted}}{\text{number of moles of itaconic acid introduced}} \%$$

$$RR = \frac{\text{number of moles of citraconic anhydride formed}}{\text{number of moles of itaconic acid introduced}} \%$$

EXAMPLE 1

Into a 50 ml reactor equipped with a mechanical two-bladed agitator, maintained under a nitrogen atmosphere, were charged:

(i) 20 ml of pseudocumene,
(ii) 2 g of itaconic acid,
(iii) 0.5 g of pyridinium p-toluenesulfonate.

The mixture was agitated and heated to 166° C. for 3 hours under atmospheric pressure.

The water produced was removed by azeotropic distillation with the pseudocumene throughout the reaction.

The product obtained was analyzed by high performance liquid chromatography.

The results obtained were as follows:
(a) TT=100%
(b) RR=90%

EXAMPLE 2

The procedure of Example 1 was repeated, except that the pyridinium p-toluenesulfonate was replaced by pyridinium itaconate, prepared in situ by the addition of 0.5 g of pyridine to the reaction medium.

After analysis, the results obtained were as follows:
(a) TT=95%
(b) RR=87%

EXAMPLE 3

The procedure of Example 1 was repeated, except that the pyridinium p-toluenesulfonate was replaced by pyraznium itaconate, prepared in situ by the addition of 0.5 g of pyrazine to the reaction medium.

After analysis, the results obtained were as follows:
(a) TT=100%
(b) RR=80%

EXAMPLE 4

The procedure of Example 1 was repeated, except that the pyridinium p-toluenesulfonate was replaced by 0.5 g of pyridinium hydrochloride.

After analysis, the results obtained were as follows:
(a) TT=95%
(b) RR=88%

EXAMPLE 5

Into a 50 $cm^3$ reactor equipped with a mechanical two-bladed agitator, there were charged:
(i) 9 ml of pseudocumene,
(ii) 10 g of itaconic acid,
(iii) 0.7 g of pyridinium p-toluenesulfonate.

The mixture was agitated and heated to 166° C. for 1 hour. The water produced was removed by azeotropic distillation.

After analysis, the results obtained were as follows:
(a) TT=99%
(b) RR90%

EXAMPLE 6

The procedure of Example 5 was repeated, but 0.4 g of pyridinium p-toluenesulfonate was used instead of 0.7 g.

After analysis, the results obtained were as follows:
(b) RR=85%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of citraconic anhydride, comprising heating itaconic acid in the presence of a catalytically effective amount of a catalyst compound, which is a product of an acid with a base with at least one of the two being an organic compound, having a pKa ranging from 4 to 10.

2. The process as defined by claim 1, said catalyst compound is a salt.

3. The process as defined by claim 2, said salt having a pKa ranging from 5 to 9.

4. The process as defined by claim 2, said salt is the in situ reaction product of said itaconic acid with the base.

5. The process as defined by claim 1, said catalyst compound having a melting point of less than 200° C.

6. The process as defined by claim 5, said catalyst compound having a melting point of up to 180° C.

7. The process as defined by claim 2, said acid is a halogenated acid, a halogenated or nonhalogenated oxyacid, a halogenated or nonhalogenated sulfonic acid, or a carboxylic acid.

8. The process as defined by claim 7, said acid is hydrochloric acid, hydrobromic acid, hydrofluoric acid, sulfuric acid, pyrosulfuric acid, perchloric acid, phosphoric acid, fluorosulfonic acid, chlorosulfonic acid, trifluoromethanesulfonic acid, methanesulfonic acid, ethanesulfonic acid, benzenesulfonic acid, a benzenedisulfonic acid, a toluenesulfonic acid, a naphthalenesulfonic acid, a naphthalenedisulfonic acid, or itaconic acid.

9. The process as defined by claim 8, said acid is hydrochloric acid, hydrobromic acid, trifluoromethanesulfonic acid, methanesulfonic acid, or itaconic acid.

10. The process as defined by claim 2, said base is ammonia, a primary, secondary or tertiary amine, or a trialkyl or triaryl phosphine.

11. The process as defined by claim 10, said base is ammonia, n-propylamine, isopropylamine, isobutylamine, n-butylamine, tertiobutylamine, n-pentylamine, 2-methylbutylamine, 3-methylbutylamine, n-hexylamine, 2-ethylhexylamine, aniline, laurylamine, cyclohexylamine, cyclopentylamine, benzylamine, guanidine, acetamidine, ethanolamine, ethylenediamine, hexamethylenediamine, N-aminoethylpyrrolidine, pyrazoline, N-aminomorpholine, N-aminopiperidine, tetraethylenepentamine, dibutylamine, dipropylamine, methylpropylamine, methylbutylamine, methylisobutylamine, methyltertiobutylamine, methylbenzylamine, ditertiobutylamine, diethanolamine, 1-methylcyclopentylamine, 1-methylcyclohexylamine, dicyclohexylamine, morpholine, imidazole, pyrrolidine, imidazolidine, piperazine, indole, triethyleneamine, tributylamine, dimethylaniline, pyridine, pyrazine, triethanolamine, tri(3,6-dioxaheptyl)amine, 1,8-diaza(5,4,0) bicyclo-7-undecene, trimethylphosphine, triethylphosphine, tri-n-propylphosphine, tri-n-butylphosphine, tricyclohexylphosphine, triphenylphosphine or tritolylphosphine.

12. The process as defined by claim 10, said base is a saturated or unsaturated nitrogenous heterocycle.

13. The process as defined by claim 12, said base pyridine or pyrazine.

14. The process as defined by claim 2, said catalyst compound is pyridinium tosylate, itaconate or hydrochloride, ammonium itaconate, or phosphinium hydrobromide.

15. The process as defined by claim 1, wherein the amount of said catalyst is from 0.1% to 30% by weight of said itaconic acid.

16. The process as defined by claim 15, wherein the amount of said catalyst compound is from 1% to 4% by weight of said itaconic acid.

17. The process as defined by claim 1, carried out in an inert organic solvent medium.

18. The process as defined by claim 17, said inert organic solvent is an aliphatic hydrocarbon, an aromatic hydrocarbon, a chlorinated aliphatic hydrocarbon, a chlorinated aromatic hydrocarbon, an ether, or a nitro compound.

19. The process as defined by claim 18, said inert organic solvent is octane, isooctane, nonane, decane, undecane, tetradecane, toluene, a xylene, ethylbenzene, a diethylbenzene, a trimethylbenzene, cumene, pseudocumene, a petroleum fraction comprising admixture of alkylbenzenes, 1,1,2- trichloroethane, pentachloroethane, 1-iodo-2-methylpropane, 1-chlorohexane, 1-chloro-2-ethylhexane, chlorobenzene, a chlorotoluene, dibutyl ether, diisobutyl ether, ethylhexylether, 1-butoxy-2-methoxyethane, 1,1-diethoxybutane, amyl ether, isoamyl ether, dipropoxymethane, phenylpropylether, mesityl oxide, nitropropane, or nitrobenzene.

\* \* \* \* \*